US00PP15651P3

(12) United States Plant Patent
Hanes et al.

(10) Patent No.: US PP15,651 P3
(45) Date of Patent: Mar. 15, 2005

(54) ***GERANIUM* PLANT NAMED 'FREE ARCRED'**

(50) Latin Name: *Pelargonium peltatum*
Varietal Denomination: Free Arcred

(75) Inventors: Mitchell Eugene Hanes, Morgan Hill, CA (US); Andreas Olbring, Hollister, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 122 days.

(21) Appl. No.: 10/641,531

(22) Filed: Aug. 14, 2003

(65) Prior Publication Data

US 2005/0039237 P1 Feb. 17, 2005

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—Jondle & Associates P.C.

(57) ABSTRACT

A *Geranium* cultivar particularly distinguished by medium green foliage with light zonation, semi-double, dark red flowers with a white bi-color patterning on large umbels, fast rooting and vigorous growth.

1 Drawing Sheet

Genus and species: *Pelargonium peltatum.*
Variety denomination: 'Free Arcred'.

BACKGROUND OF THE NEW PLANT

The present invention comprises a new and distinct cultivar of *Geranium*, botanically known as *Pelargonium peltatum,* and hereinafter referred to by the cultivar name 'Free Arcred'. The new cultivar is selected from a cross of 5651-2 a unpatented proprietary line×5146-1 a unpatented proprietary line.

'Free Arcred' is a product of a planned breeding program intended to create new *Geranium* cultivars with bi-colored dark red and white, semi-double flower form, green foliage, vigorous growth and superior cutting productivity.

The new cultivar was created in 2001 in Gilroy, Calif. and has been repeatedly asexually reproduced by cuttings in Gilroy, Calif., Guatemala and Kenya over a two-year period. It has also been trialed at Gilroy, Calif., Litchfield, Mich. and Andijk, The Netherlands. It has been found to retain its distinctive characteristics through successive propagations; and this novelty is firmly fixed.

DESCRIPTION OF PHOTOGRAPH

This new *Geranium* plant is illustrated by the accompanying photograph which shows blooms, buds, and foliage of the plant in full color, the colors shown being as true as can be reasonably obtained by conventional photographic procedures.

The photograph shows an overall plant habit; inset shows an upclose view of flowers.

DESCRIPTION OF THE NEW CULTIVAR

The following detailed descriptions set forth the distinctive characteristics of 'Free Arcred'. The data which defines these characteristics were collected from asexual reproductions carried out in Gilroy, Calif. The plant history was taken on 6 month old plants blossomed in one-gallon pots in the fall/winter season, in poly-covered greenhouse under natural light in a greenhouse and color readings were taken in the greenhouse in Gilroy, Calif. under natural light. Plants had been cut back numerous times prior to data readings taken.

Color references are primarily to The R.H.S. Colour Chart of The Royal Horticultural Society of London (R.H.S.). Texture description details were observed under a dissecting microscope.

DETAILED BOTANICAL DESCRIPTION

Classification:
*Botanical.—Pelargonium peltatum.*
*Commercial.—Ivy Geranium.*

Form: Semi upright and decumbent.
Growth and branching habit: Good vigorous habit, well branched.
Height: From soil level to top of plant (excluding blooms) 20–25 cm; from soil level to top of umbels 25–30 cm.
Width: 40–50 cm if lateral branches are outstretched the width is approximately 50–70 cm.
Time to produce a finished flowering plant: 12–14 weeks for 4–6 inch pots.
Outdoor plant performance: Good weather tolerance, used in hanging baskets, patio or mixed containers.
Time to initiate roots: 12–28 days.
Root description: White, slightly pubescent, fibrous yet coarse.

The Leaves

Color: Upper side, closest to RHS 137B (green). Underside, closest to RHS 138A (green).
Length: Full expanded leaves, 6.7–7.5 cm.
Width: Full expanded leaves 7.5–8.7 cm.
Apex description: Mucronulate.
Base description: Cordate.
Shape: Reniform.
Margin: Entire-Ciliate.
Texture: Hirsute.
Zonation color: RHS 187A.
Zonation diameter: 1.5–2.0 cm.
Venation type: Palmate.
Venation color: Closest to RHS 144B (yellow-green).
Petiole color: RHS 137B (green).
Petiole length: 4.0–6.0 cm.
Petiole diameter: 0.2 cm.
Petiole texture: Hirsute.

The Stem

Color: Closest to RHS 138A (green).
Length: 30.0–40.0 cm.
Internode length: 3.0–5.0 cm.
Texture: Hirsute.

The Bud

Diameter: 0.6–0.8 cm.
Length: 1.2–1.4 cm.
Shape: Elliptic-Oval.
Color when sepals first divide: RHS 11D (yellow) base color with RHS 45C (red) speckling and RHS 45A (red) margins.

The Inflorescence

Peduncle color: RHS 144A (yellow-green) but a little darker.
Peduncle length: 9.0–17.0 cm.
Peduncle diameter: 2.5–3.0 cm.
Peduncle texture: Hirsute.
Pedicel color: RHS 144A (yellow-green).
Pedicle length: 1.6–1.8 cm.
Pedicel diameter: 0.15 cm.
Pedicel texture: Hirsute, glandular hairs and pilose.

The Flower

Type: An umbel composed of approximately 9–16 flowers.
Blooming habit: Continuous blooming throughout the growing season. Good floriferousness.
Umbel diameter: 8.0–8.5 cm.
Umbel depth (height): 4.0–4.5 cm.
Flower form: Polypetalous; 13–15 cm mostly imbricate petals, 4–7 petaloids.
Petal/petaloid color (uppersurface): Base color of RHS N57B (white) but whiter, wide margin of between RHS 46A and B (red) with minute spots of RHS N57B (red-purple) and RHS 54B (red) of various intensities, often giving the appearance of vertical striations; upper 2–3 petals, macule of RHS 67B (red-purple), RHS 70A (red-purple) and RHS 71A (red-purple); Undersurface, RHS N155B (white) but whiter; narrow margin of RHS 46C (red); less amount of spotting of RHS N57B (red-purple).
Color change with age: Colors do not change with age but may change with temperature and lighting (culture/growing conditions).
Flower diameter: 5.0–6.0 cm.
Petal shape: Spathulate.
Petal apex shape: Rounded.
Petal base shape: Acuminate.
Petal margin: Entire.
Petal texture: Papillose.
Flower persistence: An open flower will hold its petals until the flower begins to dehisce or approximately 7–10 days.
Fragrance: No.
Number of sepals: Five, 1 larger than the other, fused at base.
Sepal color: RHS 143B and C (green).
Sepal length: 1.0–1.2 cm.
Sepal width: 0.3–0.35 cm.
Sepal shape: Linear/Lanceolate.
Sepal apex shape: Apiculate.
Sepal texture: Hirsute, glandular hairs and pilose.

The Reproductive Organs

Stamens: 6–8, sometimes fused to petaloids.
Filament color: RHS N155B(white) with slight RHS 54B (red) vertical striations.
Pollen color: RHS N170A (greyed-orange).
Pistil: 1.
Stigma color: RHS 185D (greyed-purple).
Style color: RHS 147D (yellow-green).
Fruit set: Not observed.

Disease and Insect Resistance

Less susceptibility to Oedema.

Comparison with Known Cultivars

'Free Arcred' has bicolored dark red and white flowers. Whereas 'Free Dark Red' (U.S. Plant Pat. No. 12,446) has uniform colored dark red flowers.

I claim:

1. A new and distinct cultivar of *Geranium* plant as shown and described herein.

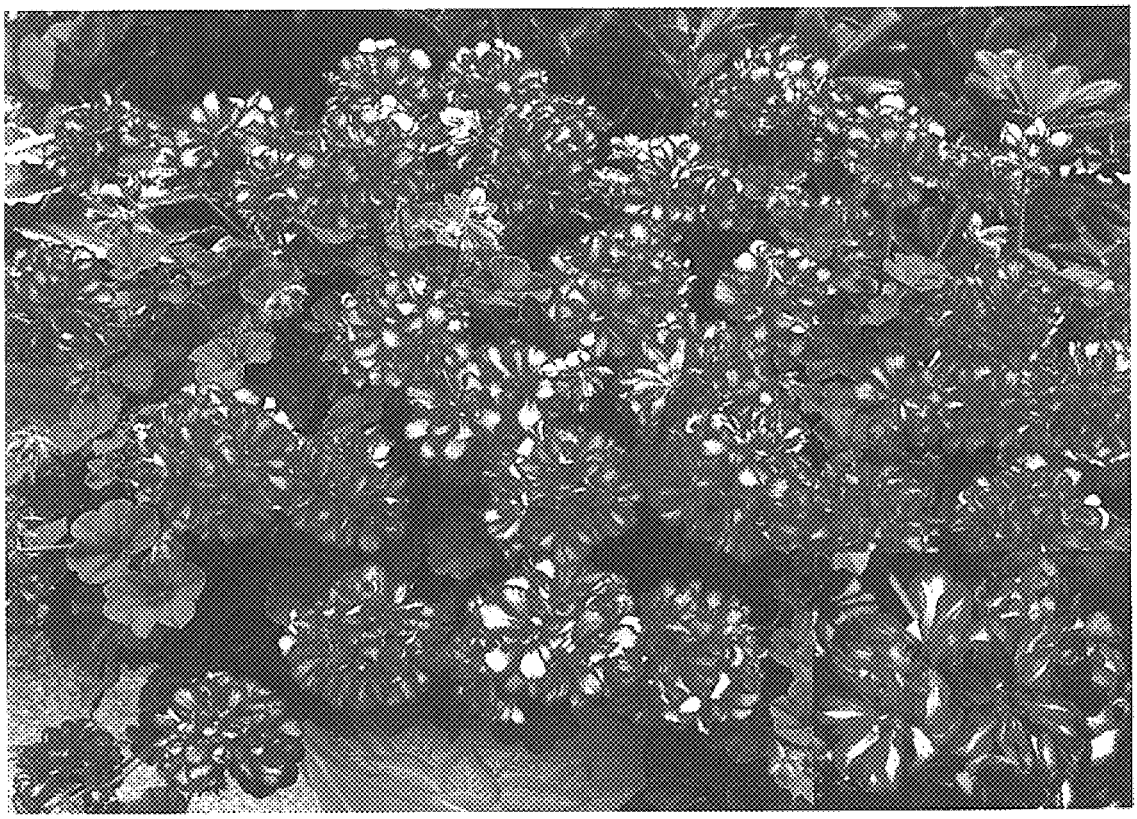

* * * * *